(12) United States Patent
Hastings et al.

(10) Patent No.: US 6,227,040 B1
(45) Date of Patent: *May 8, 2001

(54) METHOD AND APPARATUS FOR DETERMINING THE VISCOSITY OF A FLUID IN A CONTAINER

(75) Inventors: Calvin R. Hastings, Pittsburgh, PA (US); Herbert Estrada, Annapolis, MD (US); Steven J. Johnson, Pittsburgh, PA (US); Robert C. Miller, New Alexandria, PA (US); Donald R. Augenstein, Pittsburgh, PA (US)

(73) Assignee: Caldon, Inc., Pittsburgh, PA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/017,765

(22) Filed: Feb. 3, 1998

(51) Int. Cl.⁷ ............................ G01N 11/00; G01N 29/02
(52) U.S. Cl. ............................................. 73/54.41; 73/592
(58) Field of Search ............................... 73/54.41, 64.42, 73/64.53, 61.79, 592

(56) References Cited

U.S. PATENT DOCUMENTS

| 2,768,524 | * | 10/1956 | Beard ................................... 73/54.41 |
| 3,392,574 | * | 7/1968 | Lemon et al. ........................ 73/64.53 |
| 3,553,636 | * | 1/1971 | Baird ................................... 73/54.41 |
| 3,720,105 | * | 3/1973 | Cirulis . |
| 4,065,958 | * | 1/1978 | Krylova et al. . |
| 4,095,457 | * | 6/1978 | Koda et al. . |
| 4,331,025 | * | 5/1982 | Ord, Jr. . |
| 4,559,810 | * | 12/1985 | Hinrichs et al. . |
| 5,271,267 | * | 12/1993 | Baumoel ............................. 73/54.41 |
| 5,359,897 | * | 11/1994 | Hamstead et al. ..................... 73/597 |
| 5,365,778 | * | 11/1994 | Sheen et al. ........................ 73/54.41 |
| 5,433,112 | * | 7/1995 | Piche et al. ............................ 73/597 |
| 5,557,047 | * | 9/1996 | Koide .................................... 73/597 |
| 5,686,661 | * | 11/1997 | Singh et al. . |

* cited by examiner

Primary Examiner—Daniel S. Larkin
(74) Attorney, Agent, or Firm—Ansel M. Schwartz

(57) ABSTRACT

An apparatus for determining the viscosity of a fluid in a container (such as a pipe). The apparatus comprises a mechanism for transmitting a signal into a fluid in a container. The transmitting mechanism contacts the container and provides the signal to the fluid in the container. The apparatus comprises a mechanism for receiving the signal after the signal has passed through the fluid. The receiving mechanism contacts the container and receives the signal from the fluid in the container. The apparatus comprises a mechanism for determining the fluid in the container from the signal after the signal has passed through the fluid and determining the fluid viscosity from the amplitude and sound velocity. The determining mechanism is connected to the receiving mechanism. The method comprises the steps of transmitting a signal into fluid. Then there is the step of receiving the signal after it has passed through the fluid. Next there is the step of determining the attenuation of the signal as the signal has passed through the fluid. Then there is the step of finding the viscosity of the fluid in the container from the attenuation of the signal and transit time.

33 Claims, 6 Drawing Sheets

METHOD AND APPARATUS FOR DETERMINING THE VISCOSITY OF A FLUID IN A CONTAINER

FIELD OF THE INVENTION

The present invention is related to the measurement of fluid viscosity in a container, such as a drum, tank or pipe. More specifically, the present invention is related to the determination of the viscosity of a fluid in a container by determining the attenuation of an acoustic signal traveling through the fluid and the speed of sound of the fluid. The fluid may be at rest or in motion.

BACKGROUND OF THE INVENTION

In petroleum and other pipelines, there exists a need to measure certain properties of the fluid, which generally is flowing.

In particular, a measurement of viscosity (either absolute or kinematic) is needed to:

(a) differentiate fluids, (b) detect the interface between two different fluids, (c) characterize pressure gradients in a pipeline for purposes of leak detection and locations, (d) determine when a change or interface between fluids occur, and (e) determine the required amount of dilution agent to meet the maximum viscosity limit set by the pumping power and pressure rating of the pipeline.

Currently available means for these measurements are complex, expensive, and sometimes unreliable. For example, viscous forces are sometimes measured by vibratory systems. For these means and most others, a bypass line is necessary to direct a fraction of the flowing fluid to the means of measurement. The bypass can become obstructed with waxes or other elements carried by the flowing fluid. In addition, the moving parts of such measurement means can create maintenance and calibration problems. Many pipeline operators take grab samples of the flowing fluid to determine density and viscosity, because the accuracy and reliability of the on-line means do not meet their requirements. The expense of the sampling procedure is obvious. In addition, the procedure deprives the pipeline operator of the ability to monitor and control the properties continuously and in real time.

SUMMARY OF THE INVENTION

The present invention pertains to an apparatus for measuring the viscosity of a fluid in a container, such as a pipe. The apparatus comprises a mechanism for transmitting an acoustic signal through the fluid in a container. The transmitting mechanism provides the signal to the fluid in the container. The apparatus comprises a mechanism for receiving the signal after the signal has passed through the fluid. The receiving mechanism receives the signal from the fluid in the container. The apparatus comprises a mechanism for determining the fluid viscosity in the container from the signal after the signal has passed through the fluid. The determining mechanism is connected to the receiving mechanism.

The present invention pertains to a method for measuring the viscosity of a fluid in a container, such as a pipe. The method comprises the steps of transmitting a signal into fluid. Then there is the step of receiving the signal after it has passed through the fluid. Next there is the step of determining the attenuation of the signal after the signal has passed through the fluid. Then there is the step of finding the viscosity of the fluid in the pipe from the attenuation of the signal and its transit time, the latter being a measure of sound velocity in the fluid.

The mechanism may use transducers affixed to the outside of the container, such as a pipe, (i.e., external transducer) or transducers penetrating the container (i.e., wetted transducer).

BRIEF DESCRIPTION OF THE DRAWINGS

In the accompanying drawings, the preferred embodiment of the invention and preferred methods of practicing the invention are illustrated in which.

DESCRIPTION OF THE PREFERRED EMBODIMENT

Figure 1A:
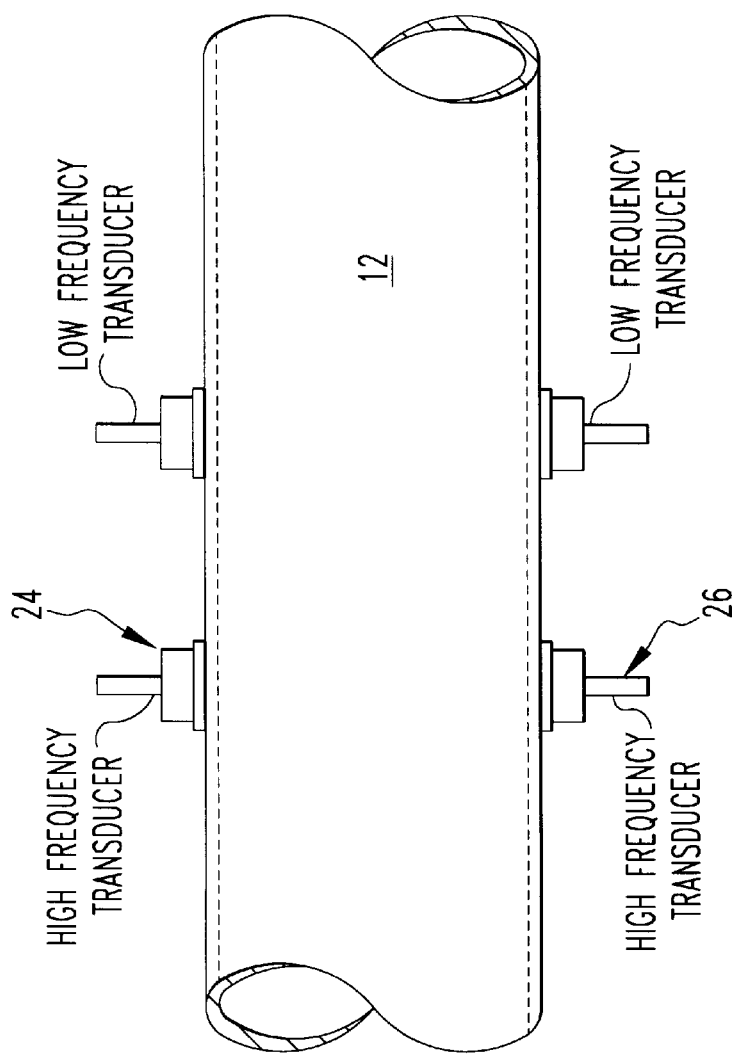
FIGS. 1a and 1b are schematic representations of side and axial views, respectively, of transducers placed on a pipe.
Figure 1B:
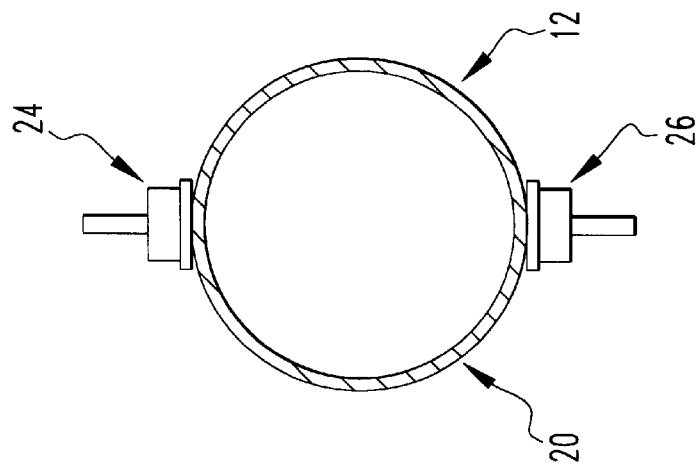

Referring now to the drawings wherein like reference numerals refer to similar or identical parts throughout the several views, and more specifically to Figure thereof, there is shown an apparatus 10 for measuring the viscosity of a fluid in a container 12, such as a pipe. The apparatus 10 comprises a mechanism 14 for transmitting a signal into a fluid 21 in a container 12. The transmitting mechanism 14 is adapted to contact the container 12 and provide the signal to the fluid 21 in the container 12. The apparatus 10 comprises a mechanism 16 for receiving the signal after the signal has passed through the fluid 21. The receiving mechanism 16 contacts the container 12 and receives the signal from the fluid 21 in the container 12. The apparatus 10 comprises a mechanism 15 for determining the viscosity of the fluid in the container 12 from the signal after the signal has passed through the fluid 21. The determining mechanism 15 is connected to the receiving mechanism 16. The determining mechanism 15 is connected to the receiving mechanism 16 and transmitting mechanism 14.

Preferably, the transmitting mechanism 14 and the receiving mechanism 16 are disposed on the external surface 18 of the pipe 12 and the signal passes from the transmitting mechanism 14 through the pipe wall 20, through the fluid 21 in the pipe 12 and through the pipe wall 20 to the receiving mechanism 16. Preferably, the transmitting mechanism 14 and the receiving mechanism 16 contact the wall of pipe 12 or penetrates pipe 12 so the signal from the transmitting mechanism 14 follows a path 22 (either diametric or diagonal) through the pipe 12 to the receiving mechanism 16. The transmitting mechanism 14 and the receiving mechanism 16 are preferably disposed on the pipe 12 opposite each other so the signal from the transmitting mechanism 14 follows a path 22 to the receiving mechanism 16. Preferably, the fluid 21 is a liquid and the transmitting mechanism 14 includes a first transducer 24 which produces an acoustic signal and the receiving mechanism 16 includes a second transducer 26 which receives the acoustic signal from the first transducer 24. The acoustic signal produced by the first transducer 24 preferably passes through the pipe wall 20 into the liquid in the pipe 12 and through the pipe wall 20 to the second transducer 26.

The transmitting mechanism 14 preferably includes a transmitter 28 which applies a first voltage signal to the first transducer 24 causing the first transducer 24 to produce the acoustic signal having frequency f. The transmitter 28 is connected to the first transducer 24. The transmitting mechanism 14 preferably includes a first voltage measuring mechanism 30 connected to the transmitter 28 which measures the voltage applied to the first transducer 24 from the transmitter 28, and records the time at which the voltage was applied.

The receiving mechanism 16 preferably includes a receiver 34 connected to the second transducer 26. The second transducer 26 converts the acoustic signal to a second voltage signal. The receiver 34 amplifies the second voltage signal from the second transducer 26. The receiving mechanism 16 preferably includes a second voltage measuring mechanism 32 connected to the receiver 34 which measures the voltage of the second voltage signal and records the time at which the voltage was received.

The determining mechanism 15 preferably includes a processor mechanism 36 which is connected to the first and second voltage measuring mechanisms 30, 32 and determines the fluid viscosity in the pipe 12 as a function of the voltage and transit time (time between transmit recorded by 30 and receive recorded by 34) measured by the first and second voltage measuring mechanism 30, 32. Preferably, the determining mechanism 15 includes a timing mechanism 32 for measuring transit time of the ultrasonic signal passing through a known distance in the liquid and wherein the processor mechanism 36 determines the liquid sound velocity. Preferably, the processor determines the viscosity as a function of the attenuation of the acoustic signal produced by the first transducer 24 and received by the second transducer 26 as it passes through a known distance in the liquid and the velocity of sound of the liquid which is determined from the transit time. Preferably, the processor determines the viscosity at the time and conditions when the acoustic signal passes through the liquid from the attenuation of the acoustic signal and the velocity of sound of the fluid at the time and the pipe 12. Preferably, the acoustic signal produced by the first transducer 24 and received by the second transducer 26 is an ultrasonic signal.

In an alternative embodiment (FIG. 5), the transmitting mechanism 14 preferably includes a transducer 24 which produces an ultrasonic signal which is sent into the liquid. The transmitting mechanism 14 preferably includes a transmitter 28 which applies a voltage signal to the transducer 24. The transmitting mechanism 14 preferably includes a voltage measuring mechanism 30 which measures the voltage applied and records the transmit time. The transmitting mechanism 14 includes a multiplexer 40 connected to the transmitter 28 and the transducer 24 that switches the first voltage signal to the transducer 24.

Preferably, the multiplexer 40 is used to time share the transducer 24 between the transmitting mechanism 14 and the receiving mechanism 16. When connected to the receiving mechanism 16, the transducer 24 converts received ultrasonic signals it receives from the fluid after the ultrasonic signals have been reflected within the pipe 12 into voltage signals. There is also a receiver 34 which receives and amplifies the voltage signals. The receiver 34 is connected to the multiplexer 40. The multiplexer 40 switches the later voltage signals from the transducer 24 to the receiver 34.

The receiving mechanism 16 preferably includes a second voltage measuring mechanism 32 connected to the receiver 34 which measures the voltage of the later voltage signal and records when the voltage was received. Preferably, the determining mechanism 15 includes a processor mechanism 36 which is connected to the first and second voltage measuring mechanisms 30, 32 and determines the fluid viscosity in the pipe 12 as a function of the voltages measured by the first and second voltage measuring mechanisms 30 and 32 and the transit time between the transmit signal recorded by 30 and the received signal recorded by 32.

Figure 2A:
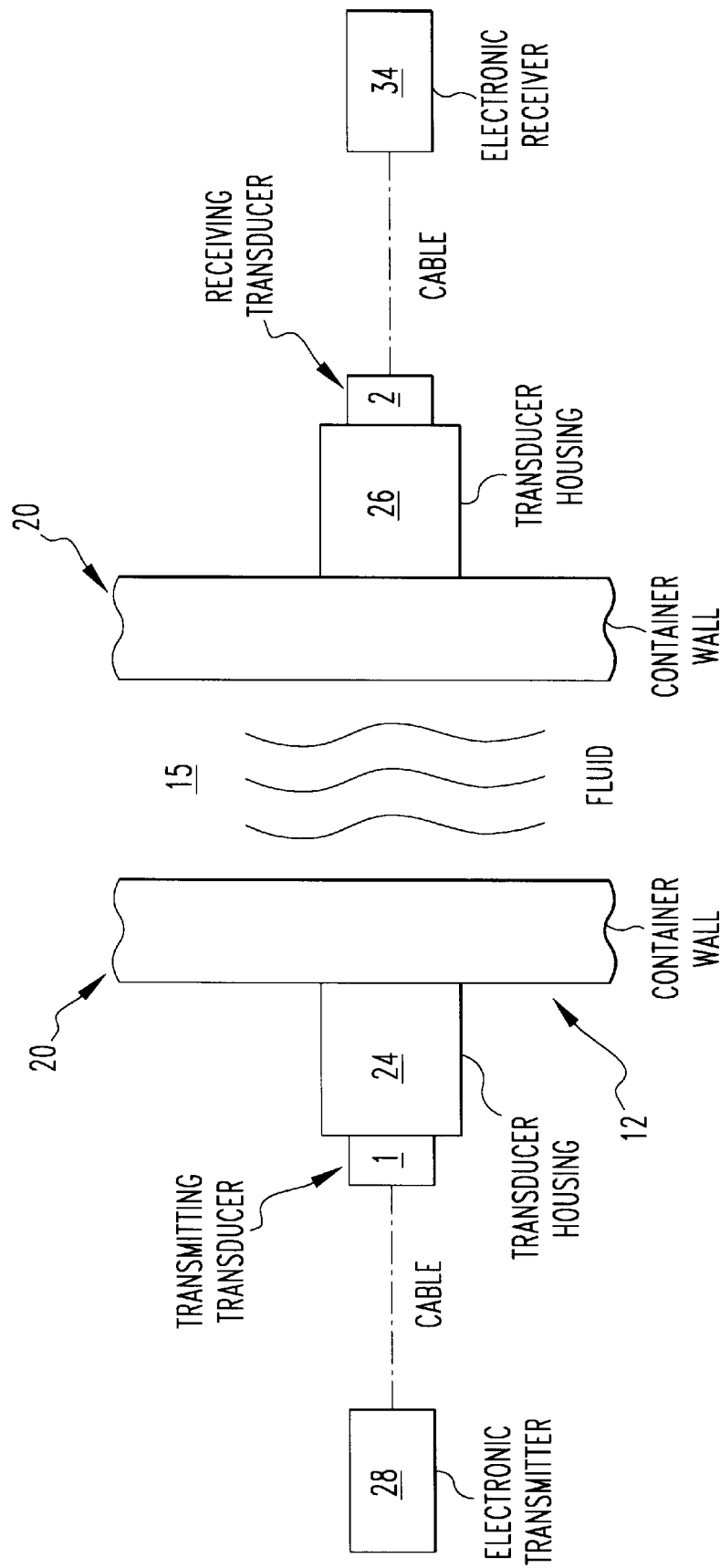
FIGS. 2a and 2b are schematic representations of the acoustic path with external transducers and wetted transducers, respectively.
Figure 2B:
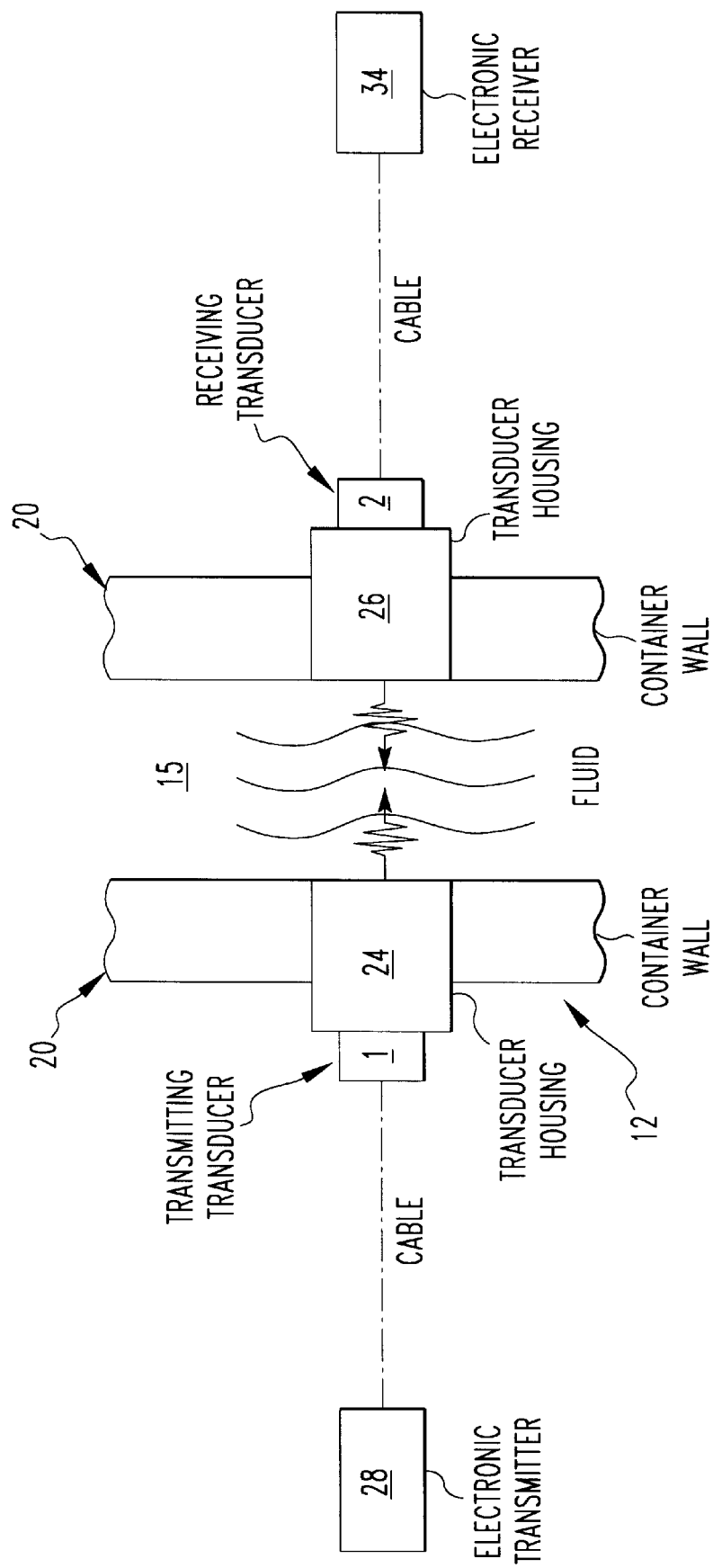
Figure 3:
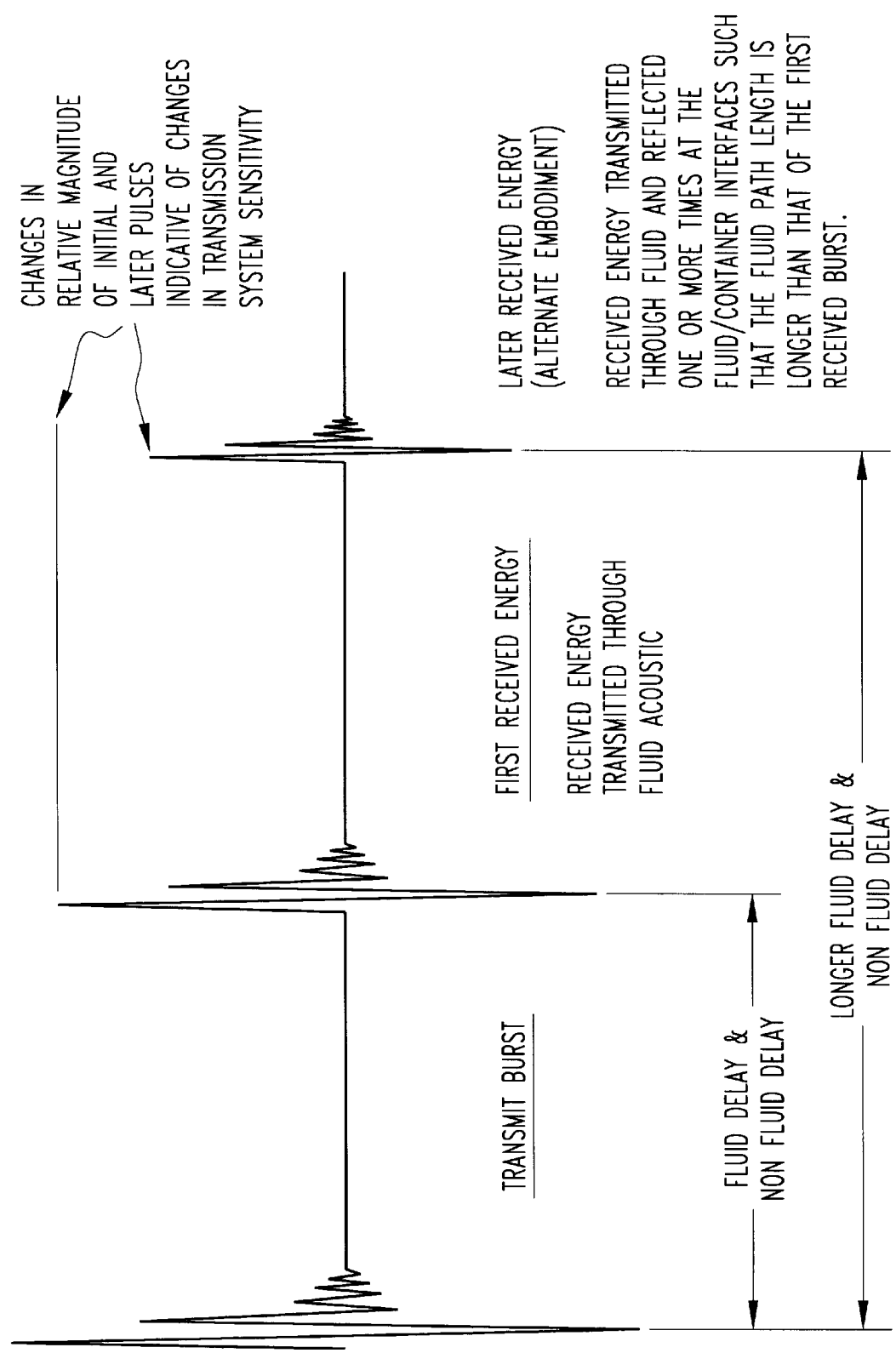
FIG. 3 is a representation of time delay and signal attenuation of a typical oscillograph regarding the present invention.

In general, an acoustic path (See FIGS. 2a and 2b) will be comprised of a number of interfaces, attenuating media and reflections as follows:

(1) Transducer 1/acoustic housing 24 interface (FIGS. 2a and 2b).
(2) Transducer housing 24 attenuation (FIGS. 2a and 2b).
(3) Transducer Housing 24/container wall 20 interface (for external transducers) (FIG. 2a).
(4) Container wall 20 attenuation (for external transducers) (FIG. 2a).
(5) Container wall 20/fluid interface (for external transducers) (FIG. 2a) and the housing 24 to fluid interface (for wetted transducers) (FIG. 2b).
(6) Fluid attenuation (FIGS. 2a and 2b)

The attenuation will depend on the fluid viscosity, the acoustic path length, and the ultrasound frequency, among other factors.

(7) Container Wall 20 Reflections (as applicable)
(8) Fluid/container wall 20 interface (for external transducers (FIG. 2a) and the fluid/housing 20 interface (for wetted transducers) (FIG. 2b).
(9) Container wall 20 attenuation (for external transducers) (FIG. 2a).
(10) Container wall 20/transducer housing 26 interface (for external transducers) (FIG. 2a).
(11) Transducer Housing 26 attenuation (FIGS. 2a and 2b).
(12) Transducer Housing 26/transducer 2 interface (FIGS. 2a and 2b).

As it makes its way from the electrical transmitter to the electronic receiver, the transmitted energy will be attenuated electrically as well as acoustically. The electrical cable, the electrical/acoustic transduction properties of the transmitting and receiving transducers, and the voltage amplification characteristics of the electronic receiver contribute to the determination of the net magnitude of the signal as measured at the electronic receiver output. There are also potential sources of attenuation due to non-ideal coupling at interfaces (1), (3), (10), and (12).

The apparatus 10 (FIGS. 4 and 5) preferably rely on the physical principles described next.

The acoustic transducer is reciprocal. When excited with voltage pulses, the transducer produces pressure waves, and when subjected to pressure waves produce a voltage. The pressure propagates from the transmitting transducer through each of the media to the receiving transducers. The apparatus 10 makes use of reflected acoustic energy as well as transmitted acoustic energy.

1. Non-Fluid Attenuation $A_{EXT}$.

The attenuation which result from a number of sources which are not dependent of the fluid contained in the pipe is referred to as $A_{EXT}$ (decibels). Included in these are the efficiency of conversion of electrical energy to ultrasonic energy and ultrasonic energy to electrical energy by the transmitting and receiving transducers, the efficiency of the coupling from the transducer to the pipe wall and pipe wall to transducer, the gain of the receiver, etc. All of these sources of attenuation are typically combined.

2. Transmitted Energy at a Media Interface, $A_{TRANS}$ and $A_{REF}$.

When acoustic energy encounters an interface between two media of differing densities and ultrasound transmission velocities, the (acoustic energy) of the transmitted wave is attenuated (decibels) according to the following equation:

$$A_{TRANS} = 10 \cdot \log\left[\frac{4\rho_2 C_2 \cdot \rho_1 C_1}{(\rho_2 C_2 + \rho_1 C_1)^2}\right] \quad \text{(Equation A)}$$

Likewise, the acoustic energy is attenuated (decibels) as follows:

$$A_{REF} = 20 \cdot \log\left[\frac{\rho_2 C_2 \cdot \rho_1 C_1}{\rho_2 C_2 + \rho_1 C_1}\right] \quad \text{(Equation B)}$$

Where:
 $\rho_i$=density of medium i
 $C_i$=propagation velocity of the ultrasound in medium i
 1=subscript for the incident medium
 2=subscript for the refracting medium
 $A_{TRANS}$=Attenuation in dB for energy transmitting through a medium interface
 $A_{REF}$=Attenuation in dB for energy reflected at a medium interface 3. Fluid Acoustic Absorption $A_{vis}$.

As ultrasonic energy travels through a viscous fluid some of the energy is dissipated in losses, the magnitude of which is related to the viscosity, the density, and the propagation velocity and frequency of the ultrasound. These losses are characterized by an attenuation constant given by a relationship of the following form:

$$\alpha = \frac{\omega^2}{2\rho C^3}(a\eta + b\eta_B) = K_V \eta \frac{\omega^2}{2\rho C^3}$$

Where:
 a=the attenuation constant in inverse length
 w=angular frequency (radians/second)
 C=propagation velocity of ultrasound (in/s)
 $\eta$=absolute shear viscosity (poise)
 $\eta_B$=absolute bulk viscosity (poise)
 $\rho$=mass density of the fluid (gm/cm$^3$)
 a,b=constants relating shear and bulk viscosity, determined by the molecular structure of the fluid. Theoretically, oil products have a=4/3 and b=1.

$$K_V = \left|a + b\frac{\eta_B}{\eta}\right| = \text{viscosity correction factor}$$

The attenuation of the acoustic energy in the viscous fluid is related exponentially to the attenuation coefficient and the distance the acoustic energy travels through the fluid. For an acoustic wave traveling across a pipe, the acoustic energy reaching the far wall is given by:

$$A_{VIS} = -35.43 \frac{K_\varpi f^2 \eta}{\rho C^3} L \quad \text{(Equation C)}$$

Where:
 $A_{VIS}$=attenuation due to viscosity losses (dB)
 L=path length

The viscosity correction factor is in general unknown and ideally is determined for all fluids that might be expected to be encountered. Practically, it may be approximated as two for most fluids that will be encountered excluding water for which it is approximately three.

4. Spreading Attenuation $A_{SPREAD}$.

Figure 6:
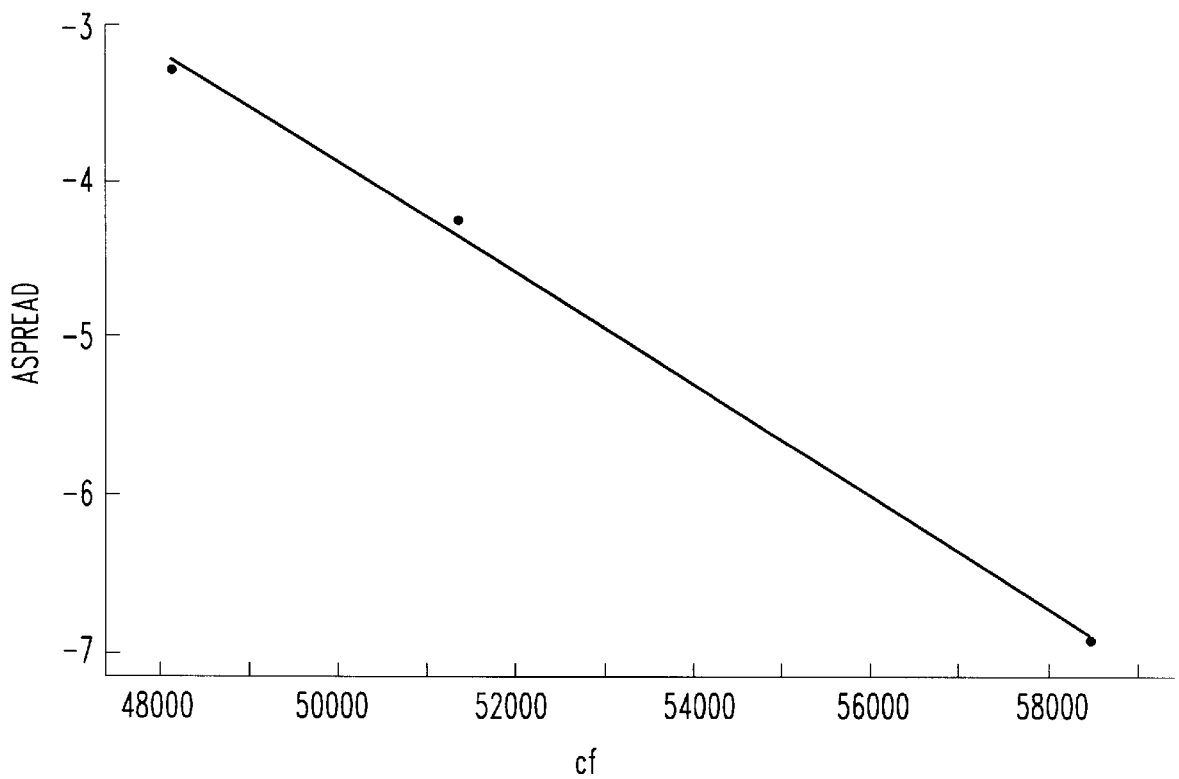
FIG. 6 is a graph of $A_{SPREAD}$ verses $C_f$.

When a beam of ultrasonic energy propagates through a media after some distance it spreads out, that is, its width increases as the distance from the source increases. Since the size of the receiving transducer is fixed, then as the distance between the transmitting and receiving transducers increases the amount of energy incident on the receiving transducer decreases. In the limit of large distance, the spreading attenuation is given by the equation $$A_{SPREAD} = 20 \cdot \text{Log}_{10}\left(\frac{f}{c_f \cdot L}\right) + K_s \quad \text{(Equation D)}$$

where
 $A_{SPREAD}$ the spreading attenuation in dB
 f, $c_f$, and L defined as before
 $K_S$=a constant dependent on the dimensions and properties of the transducer Since $K_S$ is fixed, i.e. not dependent on the fluid, it is sometimes contained in $A_{EXT}$. FIG. 6 shows the calculated dependence of the spreading attenuation on frequency for a system composed of two one inch diameter transducers mounted on pipes of various inside diameters. As can be seen, the behavior for pipes over sixteen inches ID are in reasonable agreement with the above equation for smaller size pipes there is a region where the spreading attenuation is nearly independent of the sound velocity and for smaller distances the attenuation increases as the sound velocity increases.

The apparatus 10 makes use of the dependence of the received voltage signal on the attenuation characteristics of interfaces (5) and (7) of the above list, as well as the fluid attenuation characteristic (6).

The equations describing the physical principles underlying the invention previously given show that the attenuation of the acoustic signal at the container wall/fluid interfaces is a function of the density sound velocity product for the fluid and the pipewall material.

In order to calculate the attenuation, the sound velocity in the fluid is determined using pulse transit time data measured for the acoustic path, in conjunction with delay times for the non-fluid media.

Specifically, the ultrasound velocity is given by:

$$C_f = L/t_f$$

Where:
 $t_f$=the mean transit time of acoustic pulses traveling normal to the pipe axis in the fluid
 $t_f = t_{total} - t_{non\text{-}fluid}$
 L=acoustic path length in fluid
Where:
 $t_{TOTAL}$=the total transit time from electronic transmitter through to electronic receiver.

$t_{non-fluid}$=the total of all non fluid delays including transit times for cables, transducers and housings, pipewalls and receiving electronics.

The density of the pipewall material is usually well known or can be determined before making the fluid property measurements. The sound velocity of the pipewall material is often known or, if not, can be measured using the ultrasonic thickness means. To calibrate the property measurement device for density, the density of one of the unknown fluids flowing in the pipe can be measured by means of a grab sample or determined by a sound velocity to density relationship.

The natural frequency of transmitting and receiving transducers is chosen to produce significant attenuation in the fluid itself for the full range of viscosities to be measured.

The viscosity measuring acoustic path can be calibrated by measuring the attenuation with a fluid whose viscosity is determined accurately by means of a grab sample. The viscosity of another fluid can then be determined from the attenuation measured for that fluid relative to the attenuation measured for the calibration fluid.

In one embodiment, the attenuation measurement necessary for the viscosity determination is effected by means of an automatic gain control feature applied to the receiver amplifier that processes the received acoustic pulse for amplitude and transit time determination. The automatic gain control senses the amplitude of the received signal after amplification and compares it with a preset reference. If the signal is below the reference, the gain is increased, if above the reference, the gain is decreased. The magnitude of the gain necessary to achieve this equilibrium is a direct measure of the attenuation to be measured. When the gain required for an unknown fluid is compared with the gain required with a reference fluid, the viscosity can be calculated using the relationships heretofore described.

Figure 4:
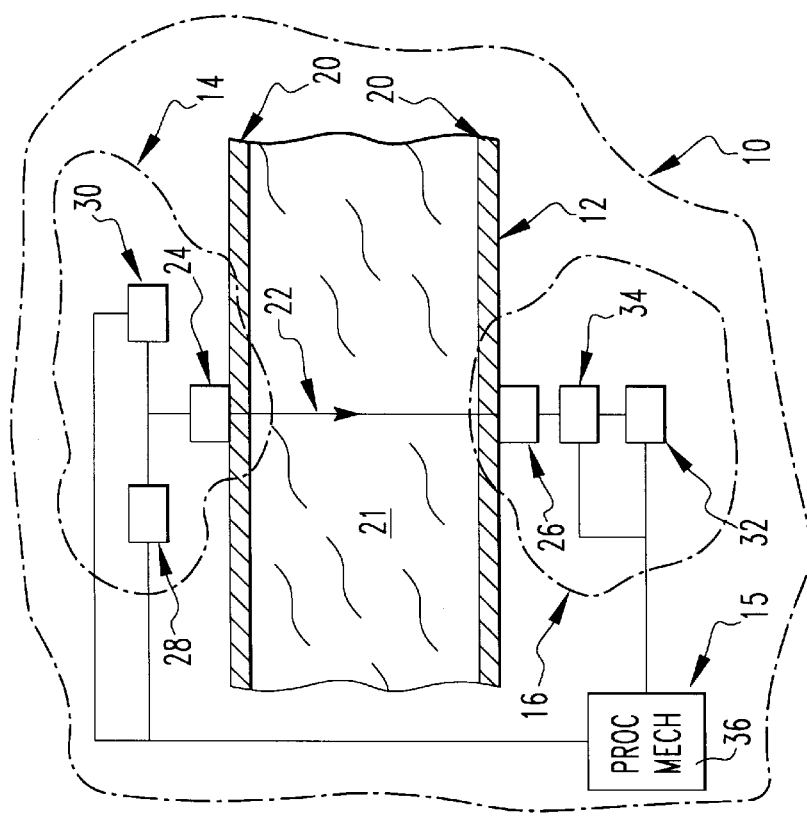
FIG. 4 is a schematic representation of the present invention.

Consider the case of two ultrasonic transducers placed at diametrically opposed positions on a length of pipe containing a fluid. As shown in FIG. 4, transmitter 28 applies a known voltage pulse to a first ultrasonic transducer 24. A first voltage measuring mechanism 30 (for example, a simple voltmeter) which measures the voltage applied to the first transducer 24. When the voltage pulse is applied to the first transducer 24, it generates an ultrasonic signal of frequency f which propagates through the pipe wall 20, fluid 21, and opposed pipe wall 20 to second transducer 26. At the second transducer 26, the ultrasonic signal is converted into an electrical signal which is amplified by the receiver 34 and connected to a second voltage measuring mechanism 32. The attenuation expressed in dB is calculated by the equation $$A_{MES} = 20 \cdot \text{Log}_{10}\left(\frac{V_1}{V_2}\right) \quad \text{(Equation E)}$$

where $V_1$ is the voltage measured by second voltage measuring mechanism 32 and $V_2$ by first voltage measuring mechanism 30. The measured attenuation $A_{MES}$ results from the sum total of all types of attenuation, namely $A_{EXT}$, $A_{TRANS}$, $A_{VIS}$, $A_{REF}$, and $A_{SPREAD}$. For an arrangement as shown in FIG. 4, the $A_{MES}$ is equal to:

$$A_{MES}=A_{EXT}+A_{VIS}+A_{SPREAD}+2 \cdot A_{TRANS} \quad \text{(Equation F)}$$

Figure 5:
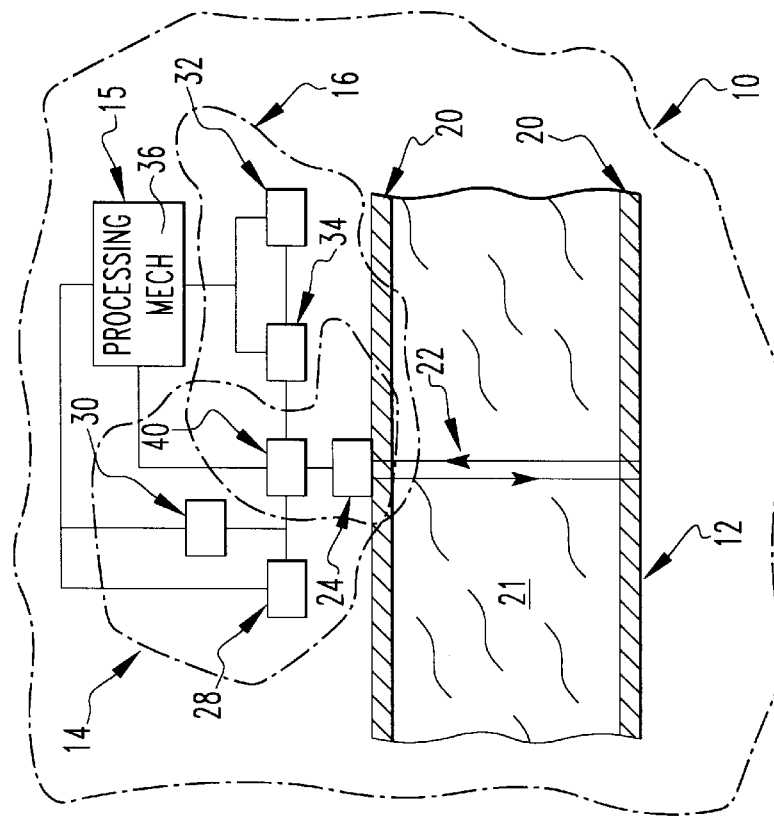
FIG. 5 is a schematic representation of an alternative embodiment of the present invention.

Another possible arrangement is to use a single transducer as shown in FIG. 5. Here, the signal voltage is measured after two passages (out and back) through the fluid and after being reflected three times by the pipe wall making four passes (out and back twice) through the fluid. In this case, the total attenuation for two passages is given by:

$$A_{MES2}=A_{EXT}+A_{VIS2}+A_{SPREAD2}+2 \cdot A_{TRANS}+A_{REF} \quad \text{(Equation G)}$$

when the pulse is detected after four passes through the fluid, the total attenuation is given by:

$$A_{MES4}=A_{EXT}+A_{VIS4}+A_{SPREAD4}+2 \cdot A_{TRANS}+3 \cdot A_{REF} \quad \text{(Equation H)}$$

Subtracting Eqs. G from H $$A_{MES4}-A_{MES2}=A_{VIS4}-A_{VIS2}+A_{SPREAD4}-A_{DPREAD2}+2 \cdot A_{REF} \quad \text{(Equation I)}$$

The advantage of this approach is that it is not necessary to determine $A_{TRANS}$ and $A_{EXT}$. Additionally, the system requires fewer transducers.

EXAMPLE 1

Determination of Viscosity Using Two Transducers Single Pass and Equation Relating Velocity of Sound and Density Three different samples of crude oil were measured in a pipeline having an inside diameter of 23.23 inches. The density of the steel from which the pipe was formed was 7.71 grams/cubic cm and its sound velocity for a compressional wave 232,437 inches/sec.

The sound velocity of these fluids were measured as described in U.S. Pat. No. 5,546,813, incorporated by reference herein, and the attenuation was measured as described above and calculated using Eq. E The following results were obtained:

| 18G | $c_f$ = 50101 inches/sec | $A_{MES}$ = −29.0 dB |
| WCH | $c_f$ = 52307 inches/sec | $A_{MES}$ = −36.4 dB |
| OCS | $c_f$ = 55452 inches/sec | $A_{MES}$ = −46.4 dB |

For this class of materials it has been determined (a number of different samples of products mentioned above were obtained and the density and velocity of sound measured. The results were plotted and fitted to a linear equation using the method of least squares) that the density in grams/cubic cm can be related to the measured velocity of sound in inches/sec by the equation $$\rho_f=0.130+0.0000144 \cdot c_f$$

In order to determine the viscosity of these fluids, it is necessary to know the value of $A_{EXT}$. Since it is difficult to determine this quantity directly, it will be estimated by using the known viscosity of one of the products. 18G was chosen for this purpose since it has the lowest total attenuation and, thus, least susceptible to errors in the measured viscosity. Further since the pipe diameter is large, Eq. D is applicable. For 18G, the measured viscosity at the temperature of the fluid in the pipe at the time the attenuation measurement was 3.43 centipoises Using the measured sound velocity, assuming $K_v$=2.0 and the equations A, D, and C, one can calculate $A_{TRANS}$=−20.83 dB $A_{SPREAD}$=−1.32 dB $A_{VIS}$=−1.32 dB and since $A_{MES}$=−29 dB it is found from Eq F that $A_{EXT}$=−6.32 dB Calculating $A_{TRANS}$ and $A_{SPREAD}$ using Eqs A & D for WCH, it is found $A_{TRANS}=-19.28$ dB $A_{SPREAD}=-1.69$ dB and then from Eq. F $A_{VIS}=-8.22$ dB and the calculated viscosity from Eq C is 63.1 centipoises. Calculating $A_{TRANS}$ and $A_{SPREAD}$ for OCS using Eqs. A & D, it is found $A_{SPREAD}=-19.28$ dB $A_{SPREAD}=-2.20$ dB and then from Eq. F $A_{VIS}=-18.60$ dB and the calculated viscosity assuming $K_v=2.0$ is from Eq. C 179.0 centipoises. This can be compared with a measured value of a sample of OCS at 180 centipoises

EXAMPLE 2

Determination of High Viscosity Using Single Transducer Four Pass Minus Two Pass and Estimation of Spreading Attenuation The difference in attenuation for four passes and two passes ($A_{MES4}-A_{MES2}$) in a short length rectangular pipe (of 9.5 inch by 5.5 inch inside dimensions) with the sound propagating parallel to the long dimension, were measured for three liquids having different velocities of sound and all having low fluid attenuation at the measuring frequency (1.0 MHZ) as a result of low viscosity, giving the ($A_{MES4}-A_{MES2}$) results Water −8.2 dB
Ethyl alcohol −4.2 dB
Kerosene −5.4 dB The properties of these materials and the calculation of the spreading attenuation is summarized using Eqs. D, B, and K in the table

|  | Water | Ethyl alcohol | Kerosene |
|---|---|---|---|
| $c_f$ inches/sec. | 58500 | 48199 | 51412 |
| $c_p$ inches/sec. | 232000 | 232000 | 232000 |
| $\rho_f$ grams/cc | 1.0 | 0.798 | 0.843 |
| $\rho_p$ grams/cc | 7.71 | 7.71 | 7.71 |
| $K_v$ | 3.1 | 2 (assumed) | 2 (assumed) |
| $\eta$ centipoise | 1.0 | 1.2 | 2.5 |
| $A_{VIS4} - A_{VIS2}$ dB | −0.104 | −0.183 | −.356 |
| $2 \cdot A_{REF}$ dB | −1.136 | −0.739 | −.789 |
| $A_{SPREAD4} - A_{SPREAD2}$ dB | −6.960 | −3.278 | −4.256 |

Using the method of least squares, the difference in spreading attenuation was fitted to the equation $$A_{SPREAD4}-A_{SPREAD2}=14.215-0.000361 \cdot c_f \quad (E2)$$

For a sample of mineral oil of unknown viscosity the measured value of $A_{MES4}-A_{MES2}$ in the same section of pipe was −21.3 dB. and the measured value of the velocity of sound was 57304 inches/sec. The measured value of the density in a separate experiment was 0.93 grams/cc. The following quantities were calculated using Eqs. B, and E2, and K $2 \cdot A_{REF}=-0.87$ dB $A_{SPREAD4}-A_{SPREAD2}=-6.42$ dB then from Eq. K $A_{VIS}=-14.0$ dB and from Eq. B and using $K_v$ of 2.84

$\eta=128$ centipoise

This can be compared to the measured value of 125–130 cS.

EXAMPLE 3

Determination of Low Viscosity Using Single Transducer Four Pass Minus Two Pass and Estimation of Spreading Attenuation The difference in attenuation for four passes and two passes ($A_{MES4}-A_{MES2}$) in a short length rectangular pipe (of 9.5 inch by 5.5 inch inside dimensions) with the sound propagating parallel to the short dimension, were measured for two liquids having different velocities of sound and having low viscosity and as a result low fluid attenuation at the measuring frequency (5.0 MHZ) giving the ($A_{MES4}-A_{MES2}$) results Water −6.3 dB
Ethyl alcohol −12.3 dB The properties of these materials and the calculation of the spreading attenuation is summarized using Eqs D, B, and K in the table

|  | Water | Ethyl alcohol |
|---|---|---|
| $c_f$ inches/sec. | 58421 | 47795 |
| $c_p$ inches/sec. | 232000 | 232000 |
| $\rho_f$ grams/cc | 1.0 | 0.798 |
| $\rho_p$ grams/cc | 7.71 | 7.71 |
| $K_v$ | 3.1 | 2.8 previously tested |
| $\eta$ centipoise | 1.0 | 1.2 |
| $A_{VIS4} - A_{VIS2}$ dB | −1.52 | −3.81 |
| $2 \cdot A_{REF}$ dB | −1.1 | −0.7 |
| $A_{SPREAD4} - A_{SPREAD2}$ | −3.66 | −7.38 |
| $f$ (frequency) | $5.0 \times 10^6$ | $5.0 \times 10^6$ |

Using a straight line fit, a spreading attenuation was fitted to the equation $$A_{SPREAD4}-A_{SPREAD2}=20 \log(0.31452-0.012025 f/c_f) \quad E3$$

For a sample of kerosene oil, the measured value of $A_{MES4}-A_{MES2}$ in the same container was 12.3 dB. and the measured value of the velocity of sound was 50848 inches/sec. The measured value of the density in a separate experiment was 0.843 grams/cc.

The following quantities were calculated using Eqs. B, and E3 and K $2 \cdot A_{REF}=-0.8$ dB $A_{SPREAD4}-A_{SPREAD2}-5.31$ dB then from Eq. K $A_{VIS4}-A_{VIS2}$ dB$=-6.17$ dB and from Eq. B $\eta=2.3$ centipoise This can be compared to the predicted value of 2.5 centipoise.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

What is claimed is:

1. An apparatus for measuring the viscosity of a flowing fluid in a pipe comprising:

a mechanism for transmitting a signal into an unknown flowing fluid in the pipe, said transmitting mechanism adapted to contact said pipe and provide the signal to the fluid in the pipe;

a mechanism for receiving the signal after the signal has passed therethrough the unknown flowing fluid and been attenuated, said receiving mechanism contacting said pipe and receives the signal from the fluid in the pipe; and a mechanism for determining the viscosity of the unknown flowing fluid in the pipe directly from the attenuated signal after the signal has passed through the fluid, said determining mechanism connected to the receiving mechanism, where attenuation of the signal is a function of $A_{EXT}$ and $A_{TRANS}$ and $A_{VIS}$ and $A_{REF}$ and $A_{SPREAD}$; and where $A_{EXT}$ is the attenuation in decibels of the signal from a number of sources which are not dependent of the flowing fluid contained in the pipe; where $A_{TRANS}$ is the attenuation in decibels for energy transmitting through a fluid interface between two media of differing densities and ultrasound transmission velocities according to the following formula:

$$A_{TRANS} = 10 \cdot \log\left[\frac{4\rho_2 C_2 \cdot \rho_1 C_1}{(\rho_2 C_2 + \rho_1 C_1)^2}\right]$$

Where:
$\rho$=density of the flowing fluid
C=propagation velocity of the signal in the fluid
1=subscript for the incident fluid
2=subscript for the refracting fluid;

$A_{REF}$ is the attenuation in decibels for energy reflected at a fluid interface according to the following formula:

$$A_{REF} = 20 \cdot \log\left[\frac{\rho_2 C_2 \cdot \rho_1 C_1}{\rho_2 C_2 + \rho_1 C_1}\right]$$

$A_{VIS}$ is the attenuation due to viscosity losses in decibels according to the following formulas:

$$\alpha = \frac{\omega^2}{2\rho C^3}(a\eta + b\eta_B) = K_V \eta \frac{\omega^2}{2\rho C^3}$$

Where:
a=the attenuation constant in inverse length
w=angular frequency (radians/second
C=propagation velocity of signal in fluid
$\eta$=absolute shear viscosity
$\eta_B$=absolute bulk viscosity
$\rho$=mass density of the fluid
a, b=constants relating shear and bulk viscosity, determined by the molecular structure of the fluid, $$K_V = \left|a + b\frac{\eta_B}{\eta}\right| = \text{viscosity correction factor}$$

$$A_{VIS} = -35.43 \frac{K_\varpi f^2 \eta}{\rho C^3} L$$

Where: L path length; and where
$A_{SPREAD}$ is the spreading attenuation in decibels according to the following formula:

$$A_{SPREAD} = 20 \cdot \log_{10}\left(\frac{f}{c_f \cdot L}\right) + K_s$$

Where:
f=frequency of signal
$C_f$ and L are defined as before
$K_s$=a constant dependent on the dimensions and properties of the transmitting mechanism.

2. An apparatus as described in claim 1 wherein the transmitting mechanism and the receiving mechanism are disposed on the external surface of the pipe and the signal passes from the transmitting mechanism through the pipe wall, through the fluid in the pipe and through the pipe wall to the receiving mechanism.

3. An apparatus as described in claim 2 wherein the transmitting mechanism and the receiving mechanism contact the pipe so the signal from the transmitting mechanism follows a path through the pipe to the receiving mechanism.

4. An apparatus as described in claim 3 wherein the fluid and the transmitting mechanism includes a first transducer which produces an acoustic signal and the receiving mechanism includes a second transducer which receives the acoustic signal from the first transducer.

5. An apparatus as described in claim 4 wherein the first transducer and second transducer diametrically oppose each other across the pipe.

6. An apparatus as described in claim 4 wherein the acoustic signal produced by the first transducer passes through the pipe wall into the fluid in the pipe and through the pipe wall to the second transducer.

7. An apparatus as described in claim 6 wherein the transmitting mechanism includes a transmitter which applies a first voltage signal to the first transducer causing the first transducer to produce the acoustic signal having frequency f, said transmitter connected to said first transducer.

8. An apparatus as described in claim 7 wherein the transmitting mechanism includes a first voltage measuring mechanism connected to the transmitter which measures the voltage applied to the first transducer from the transmitter and the time at which the voltage was applied.

9. An apparatus as described in claim 8 wherein the receiving mechanism includes a receiver connected to the second transducer, said second transducer converts the acoustic signal to a second voltage signal, said receiver amplifies the second voltage signal from the second transducer.

10. An apparatus as described in claim 9 wherein the receiving mechanism includes a second voltage measuring mechanism connected to the receiver which measures the voltage of the second voltage signal and the time at which the signal was received.

11. An apparatus as described in claim 10 wherein the determining mechanism includes a processor mechanism which is connected to the first and second voltage measuring mechanisms and determines the viscosity of the fluid in the pipe as a function of the voltage measured by the first and second voltage measuring mechanism and the transit time of the acoustic signal through the fluid.

12. An apparatus as described in claim 11 wherein the determining mechanism includes a timing mechanism for measuring transit time of the ultrasonic signal passing through a known distance in the fluid and wherein the processor mechanism determines the fluid in the pipe from the viscosity and sound velocity of the fluid.

13. An apparatus as described in claim 12 wherein the processor determines the viscosity as a function of the attenuation of the acoustic signal produced by the first transducer and received by the second transducer as the acoustic signal passes through a known distance in the fluid and the velocity of sound of the liquid which is determined from the transit time of the acoustic signal through the fluid.

14. An apparatus as described in claim 13 wherein the processor determines the viscosity at the time and conditions when the acoustic signal passes through the fluid from the attenuation of the acoustic signal and the velocity of sound of the fluid at said time and said pipe.

15. An apparatus as described in claim 14 wherein the acoustic signal produced by the first transducer and received by the second transducer is an ultrasonic signal.

16. An apparatus as described in claim 3 wherein the fluid is a liquid and wherein the transmitting mechanism includes a first transducer which produces an ultrasonic signal which is sent into the liquid.

17. An apparatus as described in claim 16 wherein the transmitting mechanism includes a transmitter which applies a first voltage signal to the first transducer and a first voltage measuring mechanism which measures the voltage applied to the first transducer from the transmitter and a multiplexer connected to the transmitter and the first transducer for controlling when the first voltage signal can pass to the first transducer.

18. An apparatus as described in claim 17 wherein the receiving mechanism also includes the first transducer which converts the ultrasonic signal the first transducer receives from the liquid after the ultrasonic signal is reflected from the pipe into a second voltage signal, and a receiver which receives the second voltage signal and amplifies the second voltage signal, said receiver connected to the multiplexer, said multiplexer controlling when the second voltage signal from the first transducer can pass to the receiver.

19. An apparatus as described in claim 18 wherein the receiving mechanism includes a second voltage measuring mechanism connected to the receiver which measures the voltage of the second voltage signal and the received time of the second voltage signal.

20. An apparatus as described in claim 19 wherein the determining mechanism includes a processor mechanism which is connected to the first and second voltage measuring mechanisms and determining the viscosity of the liquid in the pipe as a function of the voltage measured by the first and second voltage measuring mechanism and the sound velocity.

21. An apparatus as described in claim 1 wherein the transmitting mechanism and receiving mechanism penetrate through the pipe wall and contact the interior of the pipe.

22. An apparatus as described in claim 21 wherein the transmitting mechanism includes a first transducer and the receiving mechanism includes a second transducer, and the first transducer and second transducer contact the pipe such that the signal passes between them.

23. An apparatus as described in claim 1 wherein the determining mechanism determines the viscosity without any temperature measurement of the fluid.

24. An apparatus as described in claim 1 wherein the determining mechanism determines the viscosity from only the attenuation of the signal.

25. A method for measuring the viscosity of a flowing fluid in a pipe comprising the steps of:

transmitting a signal into an unknown flowing fluid in the pipe;

receiving the signal after the signal has passed through the unknown flowing fluid in the pipe and been attenuated;

determining the attenuation of the signal as the signal has passed through the unknown flowing fluid in the pipe; and finding the viscosity of the unknown flowing fluid in the pipe directly from the attenuation of the signal and the sound velocity, where attenuation of the signal is a function of $A_{EXT}$ and $A_{TRANS}$ and $A_{VIS}$ and $A_{REF}$ and $A_{SPREAD}$; where $A_{EXT}$ is the attenuation in decibels of the signal from a number of sources which are not dependent of the flowing fluid contained in the pipe; where $A_{TRANS}$ is the attenuation in decibels for energy transmitting through a fluid interface between two media of differing densities and ultrasound transmission velocities according to the following formula:

$$A_{TRANS} = 10 \cdot \log\left[\frac{4\rho_2 C_2 \cdot \rho_1 C_1}{(\rho_2 C_2 + \rho_1 C_1)^2}\right]$$

Where:

$\rho$=density of the flowing fluid

C=propagation velocity of the signal in the fluid

1=subscript for the incident fluid

2=subscript for the refracting fluid $A_{REF}$ is the attenuation in decibels for energy reflected at a fluid interface according to the following formula:

$$A_{REF} = 20 \cdot \log\left|\frac{\rho_2 C_2 \cdot \rho_1 C_1}{\rho_2 C_2 + \rho_1 C_1}\right|$$

$A_{VIS}$ is the attenuation due to viscosity losses in decibels according to the following formulas:

$$\alpha = \frac{\omega^2}{2\rho C^3}(a\eta + b\eta_B) = K_V \eta \frac{\omega^2}{2\rho C^3}$$

Where:

a=the attenuation constant in inverse length w=angular frequency (radians/second)

C=propagation velocity of signal in fluid $\eta$=absolute shear viscosity $\eta_B$=absolute bulk viscosity $\rho$=mass density of the fluid a, b=constants relating shear and bulk viscosity, determined by the molecular structure of the fluid, $$K_V = \left|a + b\frac{\eta_B}{\eta}\right| = \text{viscosity correction factor}$$

-continued $$A_{VIS} = -35.43 \frac{K_\varpi f^2 \eta}{\rho C^3} L$$

Where: L=path length; and where $A_{SPREAD}$ is the spreading attenuation in decibels according to the following formula:

$$A_{SPREAD} = 20 \cdot \log_{10}\left(\frac{f}{c_f \cdot L}\right) + K_s$$

Where:

f=frequency of signal $C_f$ and L are defined as before $K^S$=a constant dependent on the dimensions and properties of the transmitting mechanism.

26. A method as described in claim 25 wherein the transmitting step includes the step of transmitting the signal through the pipe wall into the fluid and the receiving step includes the step of receiving the signal after it has passed through the fluid and the pipe wall.

27. A method as described in claim 26 wherein the determining step includes the step of comparing the signal before the signal is transmitted through the fluid with the signal after the signal has passed through the fluid.

28. A method as described in claim 25 wherein the finding step includes the step of finding the viscosity of the fluid in the pipe directly from the attenuation of the signal and the sound velocity without any temperature measurement of the fluid.

29. A method as described in claim 25 wherein the finding step includes the step of finding the viscosity of the fluid in the pipe directly from only the attenuation of the signal and the sound velocity.

30. An apparatus for measuring the viscosity of a fluid in a pipe comprising:

a mechanism for transmitting a signal into a flowing fluid in the pipe, said transmitting mechanism adapted to contact said pipe and provide the signal to the fluid in the pipe;

a mechanism for receiving the signal after the signal has passed through the flowing fluid in the pipe and been attenuated, said receiving mechanism contacting said pipe and receives the signal from the fluid in the pipe; and a mechanism for determining the viscosity of the fluid in the pipe directly from the attenuated signal after the signal has passed through the fluid without any temperature measurement of the fluid, said determining mechanism connected to the receiving mechanism, where attenuation of the signal is a function of $A_{EXT}$ and $A_{TRANS}$ and $A_{VIS}$ and $A_{REF}$ and $A_{SPREAD}$; where $A_{EXT}$ is the attenuation in decibels of the signal from a number of sources which are not dependent of the flowing fluid contained in the pipe; where $A_{TRANS}$ is the attenuation in decibels for energy transmitting through a fluid interface between two media of differing densities and ultrasound transmission velocities according to the following formula:

$$A_{TRANS} = 10 \cdot \log\left[\frac{4\rho_2 C_2 \cdot \rho_1 C_1}{(\rho_2 C_2 + \rho_1 C_1)^2}\right]$$

Where:

ρ=density of the flowing fluid

C=propagation velocity of the signal in the fluid

1=subscript for the incident fluid

2=subscript for the refracting fluid $A_{REF}$ is the attenuation in decibels for energy reflected at a fluid interface according to the following formula:

$$A_{REF} = 20 \cdot \log\left[\frac{\rho_2 C_2 \cdot \rho_1 C_1}{\rho_2 C_2 + \rho_1 C_1}\right]$$

$A_{VIS}$ is the attenuation due to viscosity losses in decibels according to the following formulas:

$$\alpha = \frac{\omega^2}{2\rho C^3}(a\eta + b\eta_B) = K_V \eta \frac{\omega^2}{2\rho C^3}$$

Where:

a=the attenuation constant in inverse length w=angular frequency (radians/second)

C=propagation velocity of signal in fluid

η=absolute shear viscosity $\eta_B$=absolute bulk viscosity

ρ=mass density of the fluid a, b=constants relating shear and bulk viscosity, determined by the molecular structure of the fluid, $$K_V = \left|a + b\frac{\eta_B}{\eta}\right| = \text{viscosity correction factor}$$

$$A_{VIS} = -35.43 \frac{K_\varpi f^2 \eta}{\rho C^3} L$$

Where: L=path length; and where $A_{SPREAD}$ is the spreading attenuation in decibels according to the following formula:

$$A_{SPREAD} = 20 \cdot \log_{10}\left(\frac{f}{c_f \cdot L}\right) + K_s$$

Where:

f=frequency of signal $C_f$ and L are defined as before $K_s$=a constant dependent on the dimensions and properties of the transmitting mechanism.

31. A method for measuring the viscosity of a fluid identifying a fluid interface in a pipe comprising the steps of:

transmitting a signal into flowing fluid;

receiving the signal after the signal has passed through the flowing fluid and been attenuated;

determining the attenuation of the signal as the signal has passed through the flowing fluid; and finding the viscosity of the flowing fluid in the pipe directly from the attenuation of the signal and the sound velocity without any temperature measurement of the fluid, where attenuation of the signal is a function of $A_{EXT}$ and $A_{TRANS}$ and $A_{VIS}$ and $A_{REF}$ and $A_{SPREED}$; where $A_{EXT}$ is the attenuation in decibels of the signal from a number of sources which are not dependent of the flowing fluid contained in the pipe; where $A_{TRANS}$ is the attenuation in decibels for energy transmitting through a fluid interface between two media of differing densities and ultrasound transmission velocities according to the following formula:

$$A_{TRANS} = 10 \cdot \log\left[\frac{4\rho_2 C_2 \cdot \rho_1 C_1}{(\rho_2 C_2 + \rho_1 C_1)^2}\right]$$

Where:
ρ=density of the flowing fluid
C=propagation velocity of the signal in the fluid
1=subscript for the incident fluid
2=subscript for the refracting fluid $A_{REF}$ is the attenuation in decibels for energy reflected at a fluid interface according to the following formula:

$$A_{REF} = 20 \cdot \log\left[\frac{\rho_2 c_2 - \rho_1 c_1}{\rho_2 c_2 + \rho_1 c_1}\right]$$

$A_{VIS}$ is the attenuation due to viscosity losses in decibels according to the following formulas:

$$\alpha = \frac{\omega^2}{2\rho C^3}(a\eta + b\eta_B) = K_v \eta \frac{\omega^2}{2\rho C^3}$$

Where:
a=the attenuation constant in inverse length
w=angular frequency+.(radians/second
C=propagation velocity of signal in fluid
η=absolute shear viscosity
$\eta_B$=absolute bulk viscosity
ρ=mass density of the fluid
a, b=constants relating shear and bulk viscosity, determined by the molecular structure of the fluid, $$K_v = \left|a + b\frac{\eta_B}{\eta}\right| = \text{viscosity correction factor}$$

$$A_{VIS-} - 35.43 \frac{K_\omega f^2 \eta}{\rho C^3} L$$

Where: L=path length; and where $A_{SPREAD}$ is the spreading attenuation in decibels according to the following formula:

$$A_{SPREAD} = 20 \cdot \log_{10}\left(\frac{f}{c_f \cdot L}\right) + K_s$$

Where:
f=frequency of signal
$C_f$ and L are defined as before
$K_s$=a constant dependent on the dimensions and properties of the transmitting mechanism.

32. An apparatus for measuring the viscosity of a flowing fluid in a pipe comprising:

a mechanism for transmitting a signal into a flowing fluid in the pipe, said transmitting mechanism adapted to contact said pipe and provide the signal to the flowing fluid in the pipe;

a mechanism for receiving the signal after the signal has passed through the flowing fluid and been attenuated, said receiving mechanism contacting said pipe and receives the signal from the flowing fluid in the pipe; and a mechanism for determining the viscosity of the flowing fluid in the pipe directly from only the attenuated signal after the signal has passed through the flowing fluid, said determining mechanism connected to the receiving mechanism, where attenuation of the signal is a function of $A_{EXT}$ and $A_{TRANS}$ and $A_{VIS}$ and $A_{REF}$ and $A_{SPREAD}$; where $A_{EXT}$ is the attenuation in decibels of the signal from a number of sources which are not dependent of the flowing fluid contained in the pipe; where $A_{TRANS}$ is the attenuation in decibels for energy transmitting through a fluid interface between two media of differing densities and ultrasound transmission velocities according to the following formula:

$$A_{TRANS} = 10 \cdot \log\left[\frac{4\rho_2 C_2 \cdot \rho_1 C_1}{(\rho_2 C_2 + \rho_1 C_1)^2}\right]$$

Where:
ρ=density of the flowing fluid
C=propagation velocity of the signal in the fluid
1=subscript for the incident fluid
2=subscript for the refracting fluid $A_{REF}$ is the attenuation in decibels for energy reflected at a fluid interface according to the following formula:

$$A_{REF} = 20 \cdot \log\left[\frac{\rho_2 c_2 - \rho_1 c_1}{\rho_2 c_2 + \rho_1 c_1}\right]$$

$A_{VIS}$ is the attenuation due to viscosity losses in decibels according to the following formulas:

$$\alpha = \frac{\omega^2}{2\rho C^3}(a\eta + b\eta_B) = K_v \eta \frac{\omega^2}{2\rho C^3}$$

Where:
a=the attenuation constant in inverse length
w=angular frequency (radians/second)
C=propagation velocity of signal in fluid
η=absolute shear viscosity
$\eta_B$=absolute bulk viscosity
ρ=mass density of the fluid
a, b=constants relating shear and bulk viscosity, determined by the molecular structure of the fluid, $$K_v = \left|a + b\frac{\eta_B}{\eta}\right| = \text{viscosity correction factor}$$

$$A_{VIS-} - 35.43 \frac{K_\omega f^2 \eta}{\rho C^3} L$$

Where: L=path length; and where $A_{SPREAD}$ is the spreading attenuation in decibels according to the following formula:

$$A_{SPREAD} = 20 \cdot \log_{10}\left(\frac{f}{c_f \cdot L}\right) + K_s$$

Where:

f=frequency of signal $C_f$ and L are defined as before $K_s$=a constant dependent on the dimensions and properties of the transmitting mechanism.

33. A method for measuring the viscosity of a flowing fluid identifying a fluid interface in a pipe comprising the steps of:

transmitting a signal into flowing fluid;

receiving the signal after the signal has passed through the flowing fluid and been attenuated;

determining the attenuation of the signal as the signal has passed through the flowing fluid; and finding the viscosity of the flowing fluid in the pipe directly from only the attenuation of the signal and the sound velocity, where attenuation of the signal is a function of $A_{EXT}$ and $A_{TRANS}$ and $A_{VIS}$ and $A_{REF}$ and $A_{SPREAD}$; where $A_{EXT}$ is the attenuation in decibels of the signal from a number of sources which are not dependent of the flowing fluid contained in the pipe; where $A_{TRANS}$ is the attenuation in decibels for energy transmitting through a fluid interface between two media of differing densities and ultrasound transmission velocities according to the following formula:

$$A_{TRANS} = 10 \cdot \log\left[\frac{4\rho_2 C_2 \cdot \rho_1 C_1}{(\rho_2 C_2 + \rho_1 C_1)^2}\right]$$

Where:

ρ=density of the flowing fluid

C=propagation velocity of the signal in the fluid

1=subscript for the incident fluid

2=subscript for the refracting fluid $A_{REF}$ is the attenuation in decibels for energy reflected at a fluid interface according to the following formula:

$$A_{REF} = 20 \cdot \log\left[\frac{\rho_2 c_2 - \rho_1 c_1}{\rho_2 c_2 + \rho_1 c_1}\right]$$

$A_{VIS}$ is the attenuation due to viscosity losses in decibels according to the following formulas:

$$\alpha = \frac{\omega^2}{2\rho C^3}(a\eta + b\eta_B) = K_v \eta \frac{\omega^2}{2\rho C^3}$$

Where:

a=the attenuation constant in inverse length w=angular frequency (radians/second)

C=propagation velocity of signal in fluid

η=absolute shear viscosity $\eta_B$=absolute bulk viscosity

ρ=mass density of the fluid a, b=constants relating shear and bulk viscosity, determined by the molecular structure of the fluid, $$K_v = \left|a + b\frac{\eta_B}{\eta}\right| = \text{viscosity correction factor}$$

$$A_{VIS} = 35.43 \frac{K_v f^2 \eta}{\rho C^3} L$$

Where: L=path length; and where $A_{SPREAD}$ is the spreading attenuation in decibels according to the following formula:

$$A_{SPREAD} = 20 \cdot \log_{10}\left(\frac{f}{c_f \cdot L}\right) + K_s$$

Where:

f=frequency of signal $C_f$ and L are defined as before $K_s$=a constant dependent on the dimensions and properties of the transmitting mechanism.

* * * * *